US00PP18878P2

(12) United States Plant Patent
Mowrey et al.

(10) Patent No.: US PP18,878 P2
(45) Date of Patent: Jun. 3, 2008

(54) STRAWBERRY PLANT NAMED 'DRISSTRAWTWO'

(50) Latin Name: *Fragaria×ananassa*
Varietal Denomination: DrisStrawTwo

(75) Inventors: Bruce D. Mowrey, Watsonville, CA (US); Michael Ferguson, Moorpark, CA (US); JoAnne F. Coss, Salinas, CA (US); Martin P. Madesko, Watsonville, CA (US); Amado Q. Amorao, Camarillo, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 10 days.

(21) Appl. No.: 11/603,772

(22) Filed: Nov. 22, 2006

(51) Int. Cl.
*A01H 5/00* (2006.01)

(52) U.S. Cl. ..... Plt./209

(58) Field of Classification Search ..... Plt./209
See application file for complete search history.

*Primary Examiner*—Annette H Para

(74) *Attorney, Agent, or Firm*—Jondle & Associates, P.C.

(57) ABSTRACT

This invention relates to a new and distinct cultivar of strawberry plant named 'DrisStrawTwo'. The new cultivar is primarily characterized by its large fruit size, heavy fruit production, and resistance to powdery mildew.

3 Drawing Sheets

Genus and species: *Fragaria×ananassa.*
Variety denomination: 'DrisStrawTwo'.

BACKGROUND OF THE NEW PLANT

The present invention relates to a new and distinct strawberry cultivar designated 'DrisStrawTwo' and botanically known as *Fragaria×ananassa.* This new strawberry cultivar originated from a controlled cross between 'Driscoll Camarillo' (U.S. Plant Pat. No. 14,771) and 'Driscoll Marin' (U.S. Plant Pat. No. 15,375). The original seedling of the new cultivar was asexually propagated by stolons at a nursery in Shasta County, Calif. Propagules were transplanted to a controlled breeding plot in Ventura County, Calif. where it was identified and selected for further evaluation in October, 2002. 'DrisStrawTwo' was subsequently asexually propagated and underwent further testing at various locations in Monterey County, Calif. for four years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
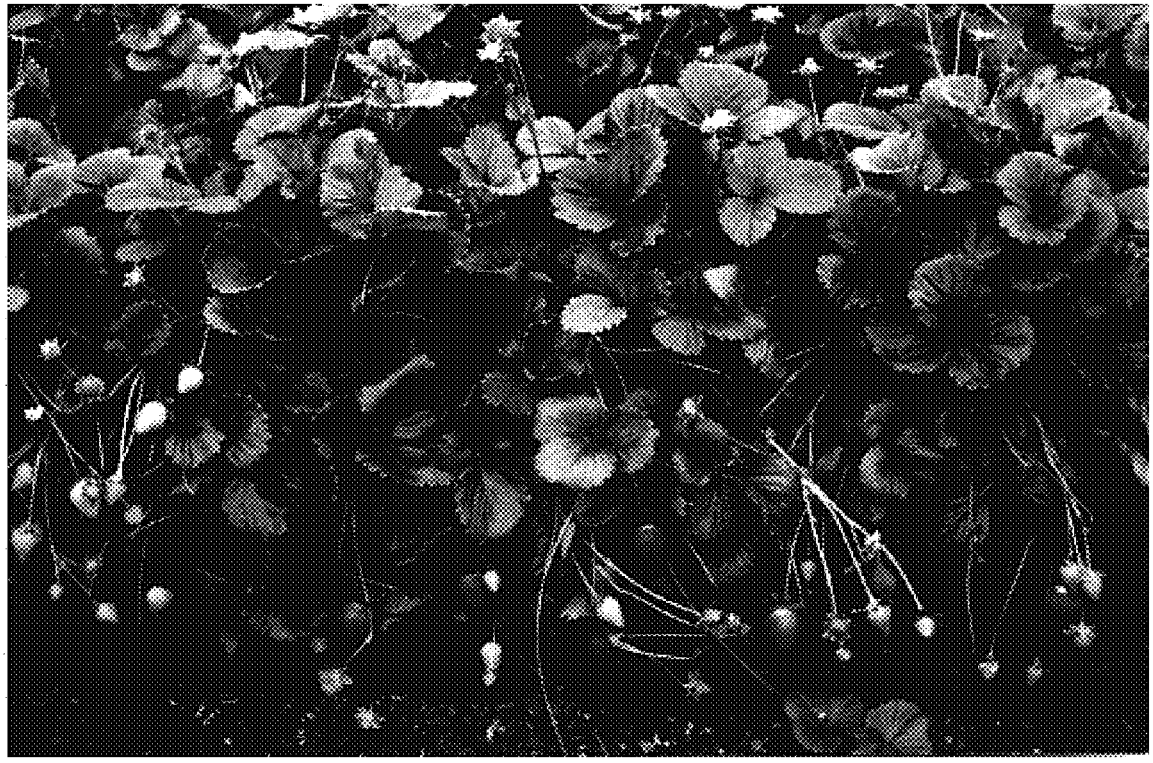
FIG. 1 shows overall plant habit including fruit at various stages of development.
Figure 2:
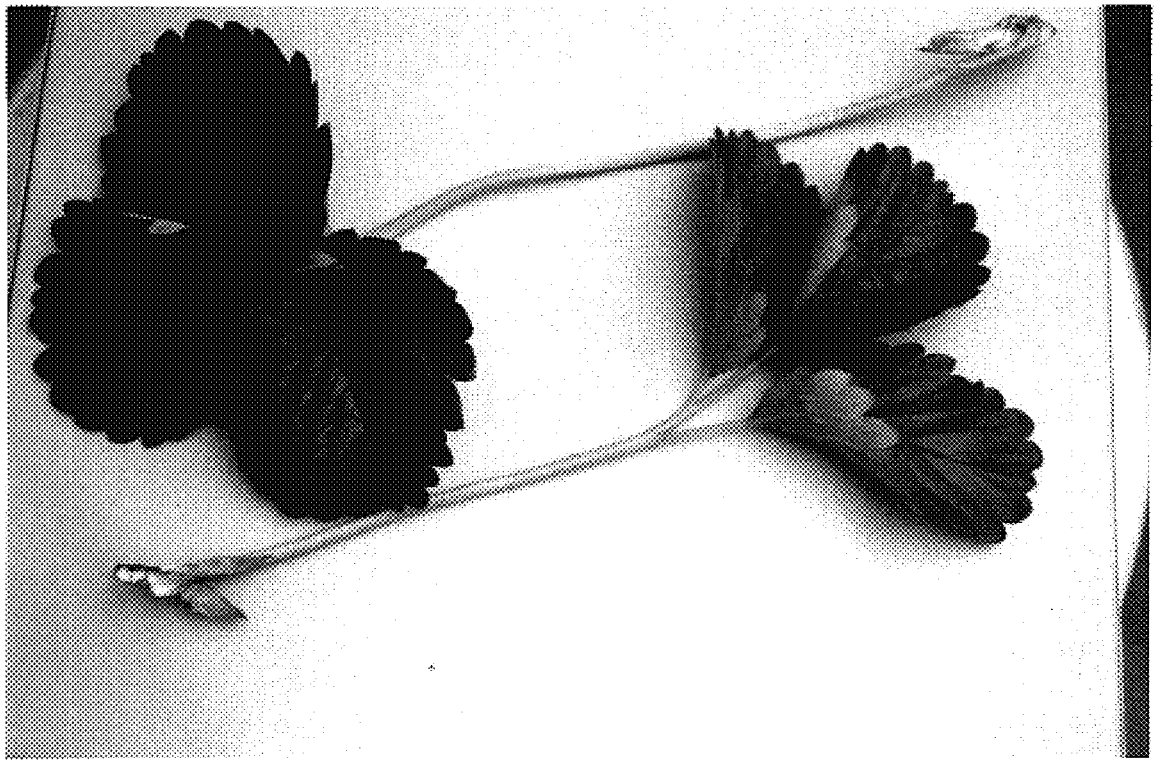
FIG. 2 shows leaves of the plant with three leaflets.
Figure 3:
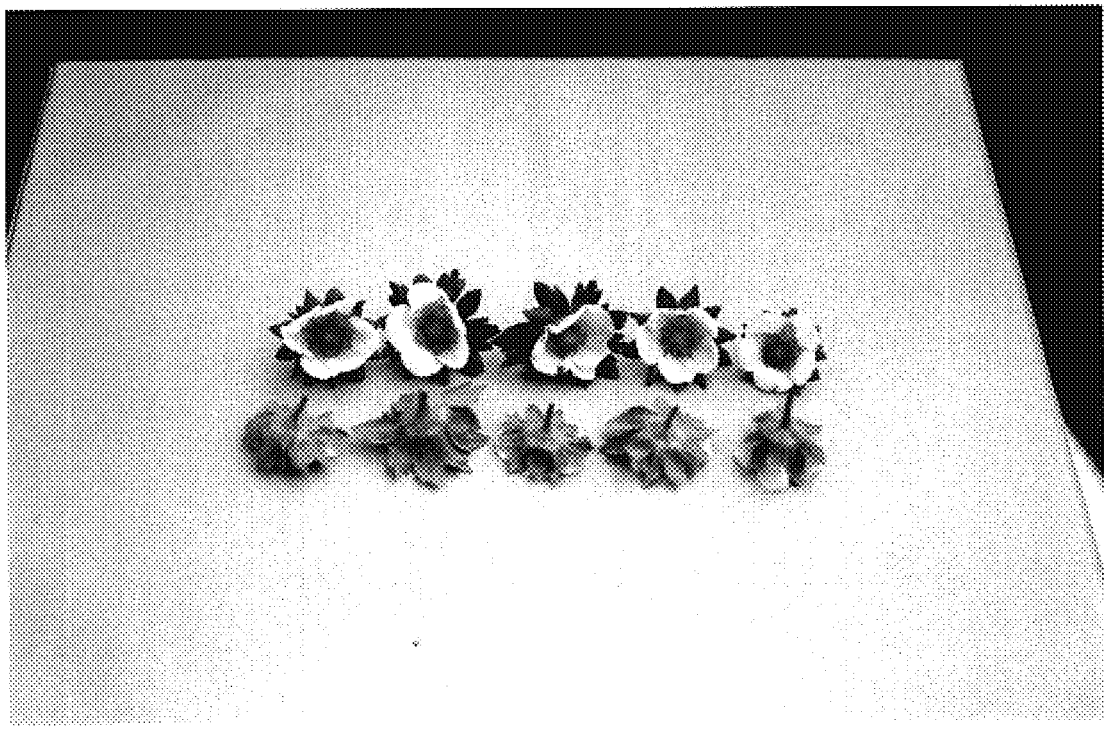
FIG. 3 shows both the upperside and underside of several of the flowers.
Figure 4:
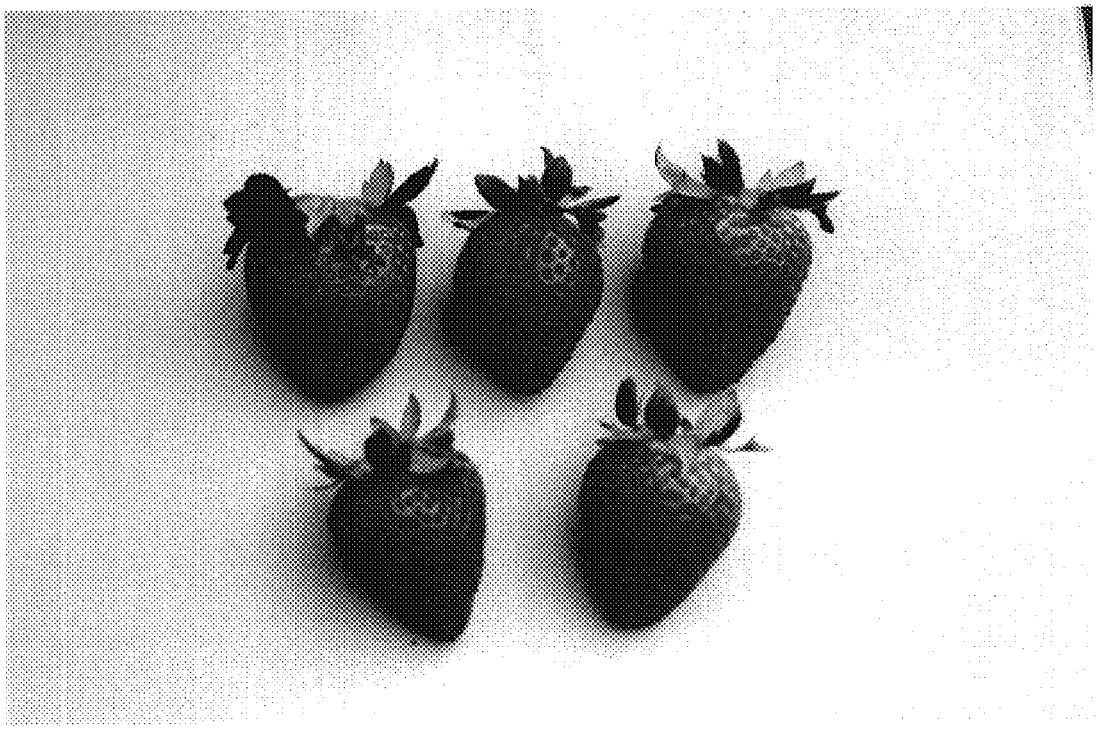
FIG. 4 shows the whole fruit.
Figure 5:
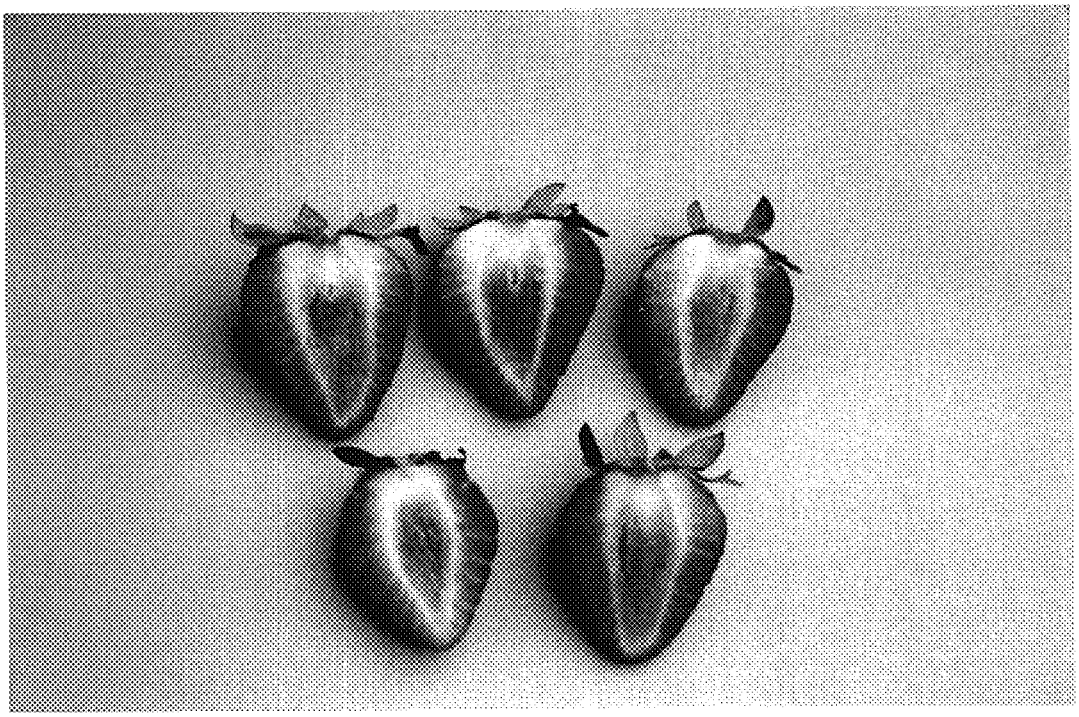
FIG. 5 shows the fruit in longitudinal cross-section.

The following description of a 10 month old plant 'DrisStrawTwo' is based on observations taken during the 2006 growing season in Monterey County, Calif. This description is in accordance with UPOV terminology. Color designations, color descriptions, and other phenotypical descriptions may deviate from the stated values and descriptions depending upon variation in environmental, seasonal, climatic and cultural conditions. 'DrisStrawTwo' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of the parents, 'Driscoll Camarillo' and 'Driscoll Marin'. Plant characteristics include plant habit, vigor, leaf shape in cross section, fruit length in centimeters, yield in grams per plant and reaction to powdery mildew.

TABLE 1

| Characteristic | 'DrisStrawTwo' | 'Driscoll Camarillo' | 'Driscoll Marin' |
|---|---|---|---|
| Habit | Flat globose | Globose | Flat |
| Vigor | Medium | Medium | Weak |
| Leaf shape in cross section | Flat | Concave | Slightly concave |
| Powdery mildew | Resistant | Between susceptible & highly susceptible | Moderately susceptible |

Table 2 shows leaf characteristics of the new cultivar compared with leaf characteristics of 'Driscoll Camarillo' and 'Driscoll Lanai' (U.S. Plant Pat. No. 15,145). Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, shape of leaf margin and shape of leaf base.

TABLE 2

| Leaf Characteristic | 'DrisStrawTwo' | 'Driscoll Camarillo' | 'Driscoll Lanai' |
|---|---|---|---|
| Terminal leaflet length (cm) | 0.76 | 0.71 | 0.76 |
| Terminal leaflet width (cm) | 0.71 | 0.75 | 0.74 |
| Terminal leaflet length/width ratio | 1.06 | 0.95 | 1.02 |
| No. teeth/terminal leaflet | 20 | 23 | 21 |
| Shape of teeth | Obtuse | Rounded | Rounded |
| Color of upperside of leaf | RHS 147A Dark yellow green | RHS 147A Dark yellow green | RHS 139A Dark green |
| Color of underside of leaf | RHS 147B Dark yellow green | RHS 138B Dark green | RHS 138B Dark green |
| Leaf shape in cross section | Flat | Concave | Between slightly concave & flat |
| Leaf blistering | Strong | Very strong | Medium |
| Leaf glossiness | Medium | Between medium & strong | Weak |
| No. leaflets | Three only | Three only | Three only |
| Terminal leaflet margin | Between revolute & flat | Between revolute & flat | Between revolute & flat |
| Terminal leaflet base shape | Rounded | Rounded | Rounded |

Table 3 shows information about the petiole, the petiolule, the bract, and the stipule of the new cultivar compared to 'Driscoll Camarillo' and 'Driscoll Lanai'. This includes petiole length in centimeters, petiole diameter in centimeters, petiolule length in centimeters, petiolule diameter in centimeters, bract frequency per petiole, stipule length in centimeters, stipule width in centimeters, stipule pubescence, petiole pubescence, pose of hairs on the petiole, color of the petiole and color of the petiolule.

TABLE 3

| Characteristic | 'DrisStrawTwo' | 'Driscoll Camarillo' | 'Driscoll Lanai' |
|---|---|---|---|
| Petiole length (cm) | 18.8 | 16.8 | 18.3 |
| Petiole diameter (cm) | 0.286 | 0.331 | 0.260 |
| Petiole pubescence | Dense | Sparse | Medium |
| Petiole pose of hairs | Outwards | Outwards | Downwards |
| Petiole color | RHS 145A Medium yellow green | RHS 149A Light yellow green | RHS 145A Medium yellow green |
| Petiolule color | RHS 145B Medium yellow green | RHS 144B Medium yellow green | RHS 145A Medium yellow green |
| Petiolule length (cm) | 1.590 | 1.376 | 1.308 |
| Petiolule diameter (cm) | 0.185 | 0.194 | 0.148 |
| Bract frequency | 0 | 0 | 0 |
| Stipule length (cm) | 3.8 | 4.0 | 3.3 |
| Stipule width (cm) | 0.794 | 0.866 | 0.550 |
| Stipule pubescence | Sparse | Sparse | Between medium & dense |

Table 4 shows stolon characteristics of the new cultivar compared to 'Driscoll Camarillo' and 'Driscoll Lanai'. These characteristics include the number of stolons, the anthocyanin coloration of the stolons, the thickness of the stolons, the pubescence of the stolons, and the average number of daughter plants.

TABLE 4

| Characteristic | 'DrisStrawTwo' | 'Driscoll Camarillo' | 'Driscoll Lanai' |
|---|---|---|---|
| Stolon Number | Medium | Medium | Many |
| Stolon Anthocyanin | Strong | Medium | Strong |
| Stolon Thickness | Thin | Between Medium & Thick | Between Medium & Thick |
| Stolon Pubescence | Sparse | Medium | Dense |
| Average Number of Daughter Plants (Nursery Average) | 17 | N/A | 67 |

Table 5 shows inflorescence characteristics of the new cultivar compared to 'Driscoll Camarillo' and 'Driscoll Lanai'. These characteristics include inflorescence position relative to foliage, relative flower size, flower diameter in centimeters (measured from petal tip to petal tip), relative spacing of petals, petal length in centimeters, petal width in centimeters, petal length to width ratio, petal color, calyx diameter in centimeters (measured on back of flower from sepal tip to sepal tip), diameter of calyx relative to corolla, diameter of inner calyx relative to outer, sepal length in centimeters (measured from sepal tip to point of attachment to receptacle), sepal width in centimeters, receptacle color and anther color.

TABLE 5

| Characteristic | 'DrisStrawTwo' | 'Driscoll Camarillo' | 'Driscoll Lanai' |
|---|---|---|---|
| Inflorescence position relative to foliage | Above | Above | Between level with & above |
| Flower size | Medium | Medium | Medium |
| Flower diameter (cm) | 2.549 | 2.698 | 2.518 |
| Petal spacing | Overlapping | Overlapping | Overlapping |
| Petal length (cm) | 1.156 | 1.275 | 1.103 |
| Petal width (cm) | 1.197 | 1.367 | 1.146 |
| Petal length/width ratio | 0.97 | 0.93 | 0.96 |
| Petal color | RHS 155D White | RHS 155B White | RHS 155C White |
| Calyx diameter (cm) | 3.260 | 3.236 | 3.469 |
| Calyx diameter relative to corolla | Larger | Between smaller & same size | Between same size & larger |
| Inner calyx diameter relative to outer | Between same size & larger | Same size | Larger |
| Sepal length (cm) | 1.108 | 1.118 | 1.187 |
| Sepal width (cm) | 0.608 | 0.709 | 0.630 |
| Receptacle color | RHS 2A Yellow | RHS 1A Green yellow | RHS 1B Green yellow |
| Anther color | RHS 15B Yellow orange | RHS 17A Yellow orange | RHS 9A Yellow orange |

Table 6 shows fruit characteristics of the new cultivar compared to 'Driscoll Camarillo' and 'Driscoll Lanai'.

TABLE 6

| Characteristic | 'DrisStrawTwo' | 'Driscoll Camarillo' | 'Driscoll Lanai' |
|---|---|---|---|
| Fruiting truss length (cm) | 31.6 | 27.6 | 24.0 |
| Fruiting truss attitude | Prostrate | Prostrate | Prostrate |
| Fruit length (cm) | 4.51 | 3.59 | 3.63 |
| Fruit width (cm) | 3.59 | 3.29 | 3.48 |

TABLE 6-continued

| Characteristic | 'DrisStrawTwo' | 'Driscoll Camarillo' | 'Driscoll Lanai' |
|---|---|---|---|
| Fruit length/width ratio | 1.26 | 1.09 | 1.04 |
| Fruit weight (g) | 24.7 | 20.6 | 24.2 |
| Relative fruit size | Large | Between medium & large | Medium |
| Predominant fruit shape | Conical | Cordate | Between conical & ovoid |
| Difference in shape between primary & secondary fruits | Moderate | Slight | Slight |
| Band without achenes | Medium | Absent or very narrow | Between narrow & medium |
| Unevenness of fruit surface | Absent or very weak | Weak | Weak |
| Fruit skin color | RHS 45A Red | RHS 46A Red | RHS 45B Orange red |
| Evenness of fruit color | Even | Even | Even |
| Fruit glossiness | Strong | Strong | Strong |
| Insertion of achenes | Between level with surface & above surface | Below surface | Level with surface |
| Achene coloration - sunward side of berry | RHS 179A Greyed red | RHS 184B Greyed purple | RHS 185B Greyed purple |
| Achene coloration - shaded side of berry | RHS 3A Yellow | RHS 13B Yellow | RHS 154B Yellow green |
| Achenes per berry | 233.7 | 224 | 226.8 |
| Insertion of calyx | Set above fruit | In a basin | Level |
| Pose of calyx segments | Between spreading & reflexed | Reflexed | Between spreading & reflexed |
| Size of calyx in relation to fruit | Smaller | Smaller | Smaller |
| Adherence of calyx | Medium | Strong | Strong |
| Firmness of flesh | Firm | Firm | Medium |
| Evenness of flesh color | Even | Slightly uneven | Uneven |
| Color of flesh | RHS 44C & RHS 155B Orange red & white | RHS 34B & RHS 155A Orange red & white | RHS 47C Orange red |

TABLE 6-continued

| Characteristic | 'DrisStrawTwo' | 'Driscoll Camarillo' | 'Driscoll Lanai' |
|---|---|---|---|
| Hollow center | Absent | Between absent & small | Medium |
| Sweetness | Medium | Medium | Medium |
| Texture when tasted | Medium | Medium | Fine |
| Harvest maturity | Mid-season | Between early & mid-season | Late |
| Type of bearing | Fully everbearing | Fully everbearing | Partially everbearing |
| Grams of fruit/plant | 1,654.7 | 1,485.1 | 1,420.4 |

Table 7 shows pest and disease characteristics of the new cultivar compared to 'Driscoll Camarillo' and 'Driscoll Lanai'.

TABLE 7

| Pest or Disease | 'DrisStrawTwo' | 'Driscoll Camarillo' | 'Driscoll Lanai' |
|---|---|---|---|
| *Tetranychus urticae* (2-spotted spider mite) | Susceptible | Moderately Susceptible | Susceptible |
| *Lygus hesperus* (Lygus bug) | Susceptible | Susceptible | Susceptible |
| Botrytis fruit rot | Moderately Susceptible | Between moderately resistant & moderately susceptible | Susceptible |
| Powdery mildew | Resistant | Between susceptible & highly susceptible | Susceptible |
| Verticillium wilt | Susceptible | Moderately Susceptible | Moderately resistant |
| Strawberry mottle virus | Moderately resistant | Moderately resistant | Moderately resistant |
| *Xanthomonas fragariae* | Moderately Susceptible | Moderately resistant | Moderately Susceptible |

We claim:

1. A new and distinct cultivar of strawberry plant as described and shown herein.

* * * * *